United States Patent [19]

Dorr

[11] Patent Number: 5,488,867
[45] Date of Patent: Feb. 6, 1996

[54] STRIP MEASURING AND CENTERING SYSTEM

[75] Inventor: John A. Dorr, Crofton, Md.

[73] Assignee: Xecutek Corporation, Annapolis, Md.

[21] Appl. No.: 932,203

[22] Filed: Aug. 21, 1992

[51] Int. Cl.$^6$ .................................................. G01N 29/22
[52] U.S. Cl. ............................................. 73/597; 73/159
[58] Field of Search .......................... 73/597, 598, 159, 73/611

[56] References Cited

U.S. PATENT DOCUMENTS

| | | | |
|---|---|---|---|
| 3,315,520 | 4/1967 | Carnevale et al. | 73/597 |
| 3,332,279 | 7/1967 | Tompos et al. | 73/159 |
| 3,570,624 | 3/1971 | O'Connor | 73/159 |
| 3,986,389 | 10/1976 | Mesina et al. | 73/611 |
| 4,404,634 | 9/1983 | Bautz | 73/159 |
| 5,126,946 | 6/1992 | Ko | 73/159 |

OTHER PUBLICATIONS

McGraw-Hill Encyclopedia of Physics, edited by Sybil P. Parker (1983) pp. 239, 240, and 1059–1060.
Concise Dictionary of Physics and related subjects by J. Thewlis (Second Edition, 1979) pp. 96, 281 and 282.

*Primary Examiner*—Hezron E. Williams
*Assistant Examiner*—Rose M. Finley
*Attorney, Agent, or Firm*—Jim Zegeer

[57] ABSTRACT

A system for locating the edges of a moving strip of material having two edges. In one embodiment, a pair of ultrasonic transducers are positioned above the path of the moving strip and oriented at acute angles relative to the surface of the strip. A circuit for causing each of the transducers to emit ultrasonic pulses in the direction of the two edges, respectively, a detector circuit connected to the ultrasonic transducers detects acoustic diffractions caused by the edges, respectively, and compares the times of detection of the acoustic diffractions to locate the positions of the edges relative to the pair of transducers. A microprocessor controls operation of the transducer and receiving signals therefrom and computes one or more of the following quantities: 1) the distance $D_1$ from the transducer to the near one of said two edges, 2) the distance $D_2$ from the transducer to the other of the two edges, 3) the distance to the center of the strip from the transducer $D_c=\frac{1}{2}(D_1+D_2)$, and 4) the width of the strip $W'=D_2-D_1$.

7 Claims, 4 Drawing Sheets

FIG. 4A
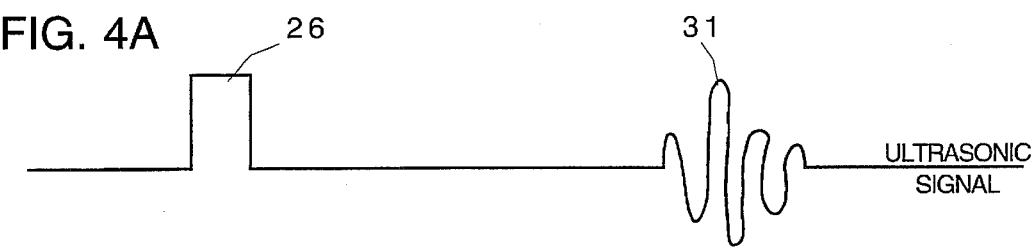
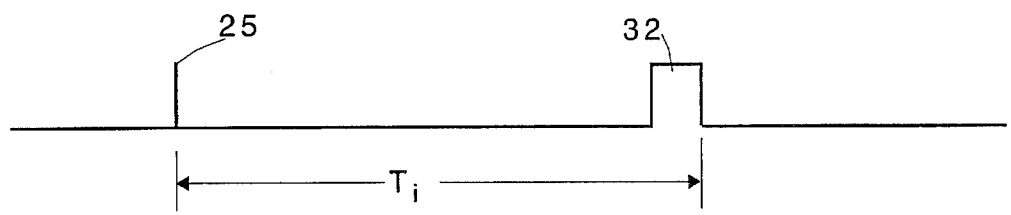
FIG. 4B
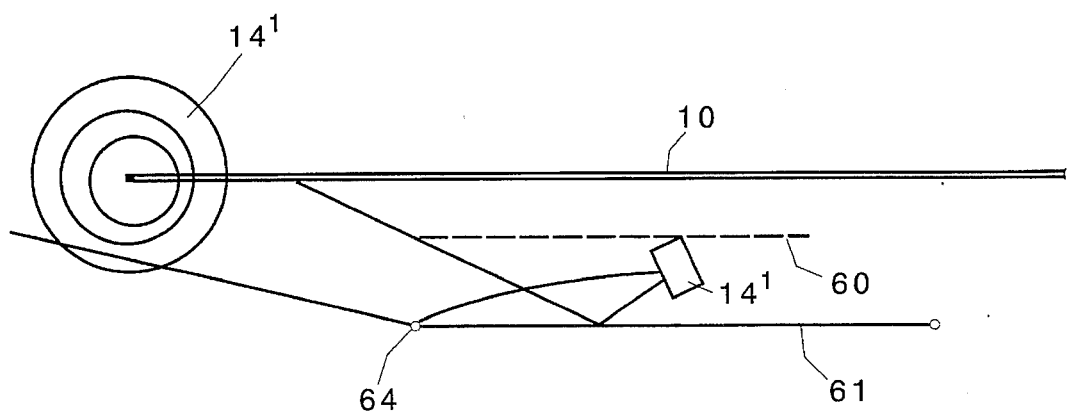
FIG. 5

5,488,867

STRIP MEASURING AND CENTERING SYSTEM

BACKGROUND AND BRIEF DESCRIPTION OF THE INVENTION

This invention relates to an ultrasonic system for locating the edges of a moving strip web or sheet of material, particularly a moving steel strip, and adjusting the strip, center the strip relative to a longitudinal axis.

In steel rolling and sheet finishing mills it is desirable to center a steel strip on a given longitudinal axis and to maintain it on the given longitudinal axis for further processing such as cutting, shaping, galvanizing, annealing, etc. In the past, mechanical sensors have been used to locate and position the strip. These mechanical systems are slow, and in high speed mills, a large section of strip can pass before corrective action can be taken. More recently, optical edge detectors have been used but these are relatively expensive systems which are frequently disabled or rendered less reliable by dirt, oil, moisture, etc. and they usually require a device or surface below or underneath the strip.

The object of the present invention is to provide an inexpensive strip edge sensor, particularly for sensing a moving strip, and still more particularly, a moving steel strip and which needs nothing underneath the strip and which operates in difficult ambient environments such as dust, moisture, oil drips, etc. A further object of the invention is to provide an edge sensing system for steel strip and for detecting changes in the position of said edges and maintaining the center of the moving steel strip on a predetermined longitudinal axis.

According to the invention, a pair of ultrasonic transducers is mounted above the center of the path of the moving strip. The transducers are oriented at an acute angle $\propto$ relative to the plane of the sheet so that, while ultrasonic reflections from the surface are away from the transducer, the edges are an acoustic discontinuity so that an acoustic pulse in a beam insonifies the edge and, hence, provide an acoustic diffraction which can be detected by the transducers to thereby locate the edges. The speed of sound in the medium is not a factor involved in the centering function. If the speed of sound is known, an ultrasonic height measurement can be made and using the signal times of the edges, a computation of the width of the moving sheet made therefrom. Moreover, when used in a steel sheet processing mill where there is dust, dirt, moisture, oil drippings, etc., the system can be used advantageously to maintain the position of the strip centered along a given axis. The system will produce high accuracy on any smooth sheet. Degradation will occur when roughness dimensions of the sheet become appreciable compared to the wavelength of the ultrasonic signal. With a rough surface, energy will be back-scattered from the surface to the transducer and will interfere with reception of the diffraction signal with resultant timing error.

DESCRIPTION OF THE DRAWINGS

The above and other objects advantages and features of the invention will become more apparent when considered with the following specification and accompanying drawings wherein:

FIG. 5 illustrates an alternative arrangement for the placement of the ultrasonic transducer shown in FIGS. 1 and 2.

DETAILED DESCRIPTION OF THE INVENTION

Figure 2:
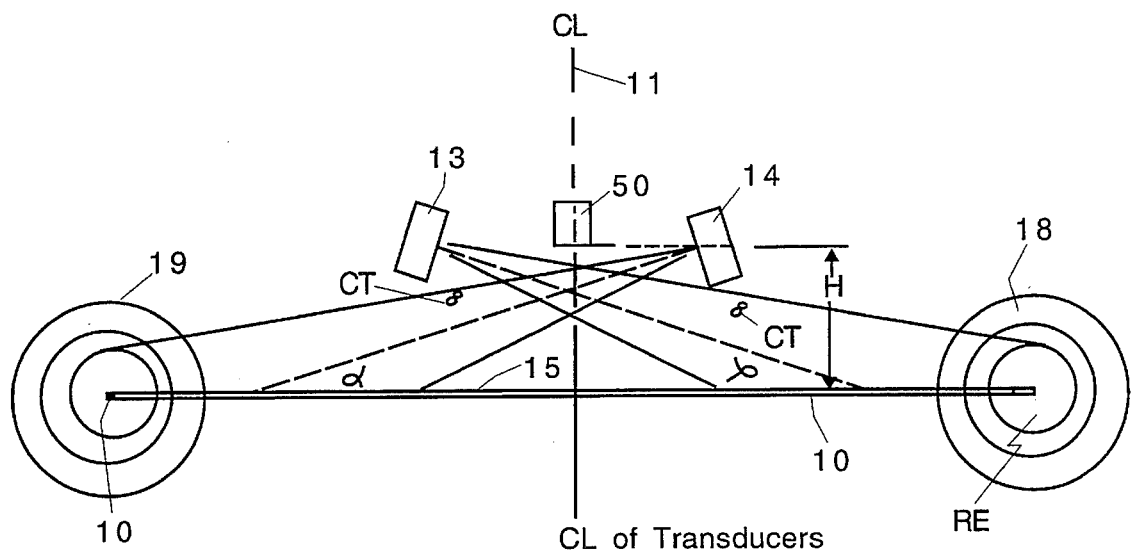
FIG. 2 is a diagrammatic elevational view.
Figure 1:
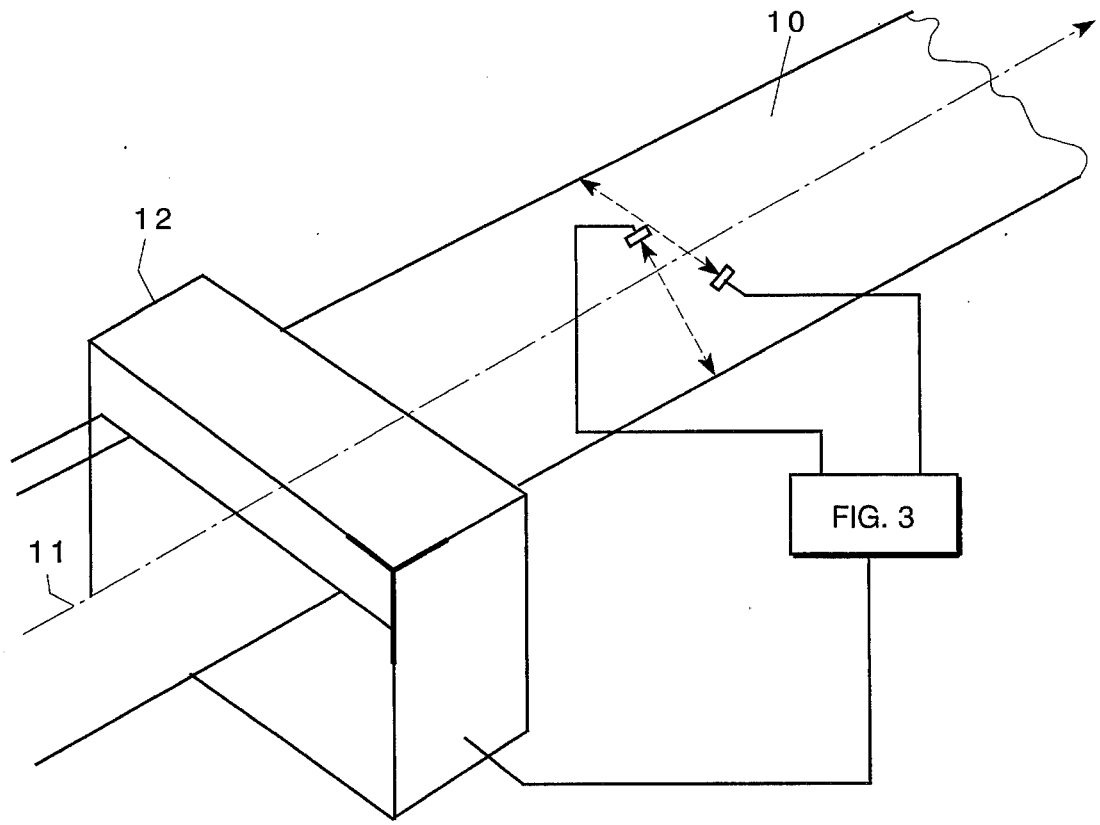
FIG. 1 is a diagrammatic perspective view of a portion of a steel strip processing mill incorporating the invention.

The invention is based on the fact that the edge of a solid object, such as a sheet of steel, constitutes an acoustic discontinuity. Ultrasonic pressure wave from a transducer directed toward the surface at an acute angle are reflected in direction away from the transducer, but at the acoustic discontinuity, the pressure wave are diffracted with a small portion thereof being returned to the transducer. This phenomena is incorporated in the embodiment of the invention shown in the drawings. Referring to FIGS. 1 and 2, a strip of material, such as steel 10 is moving along a longitudinal path having a centerline 11 and the position of the steel strip 10 relative to centerline 11 is adjustable by electrically controllable adjustment mechanism 12. In this embodiment of the invention, a pair of ultrasonic transducers 13 and 14 are mounted at acute angles a relative to the upper surface 15 of strip 10. Smaller angles produce better results.

Transducers 13 and 14 are spaced equal (or known) distances from centerline 11 and are preferably at the same angle, but they need not necessarily be in the same plane. In FIG. 2, transducer 13 is oriented toward the right edge RE and transducer 14 is oriented toward the left edge LE of strip 10. The beams from the transducers therefore insonify the edges LE and RE, respectively. Steel strip 10 is a good specular reflector of ultrasonic energy and due to the acute angle of orientation of the transducers, there is insignificant reflections back to the transducers from the surface of the strip. However, at the edges RE and LE, the ultrasonic pressure wave encounters or see a significant acoustic discontinuity and are diffracted (symbolized by concentric circles 18 and 19) or deflected thereby so that some of the ultrasonic energy is returned back to the transducers: diffraction at right edge RE returns some of the ultrasonic energy back to its source transducer 13 and diffraction at left edge LE returns some of the ultrasonic energy back to its source transducer 14.

Figure 3:
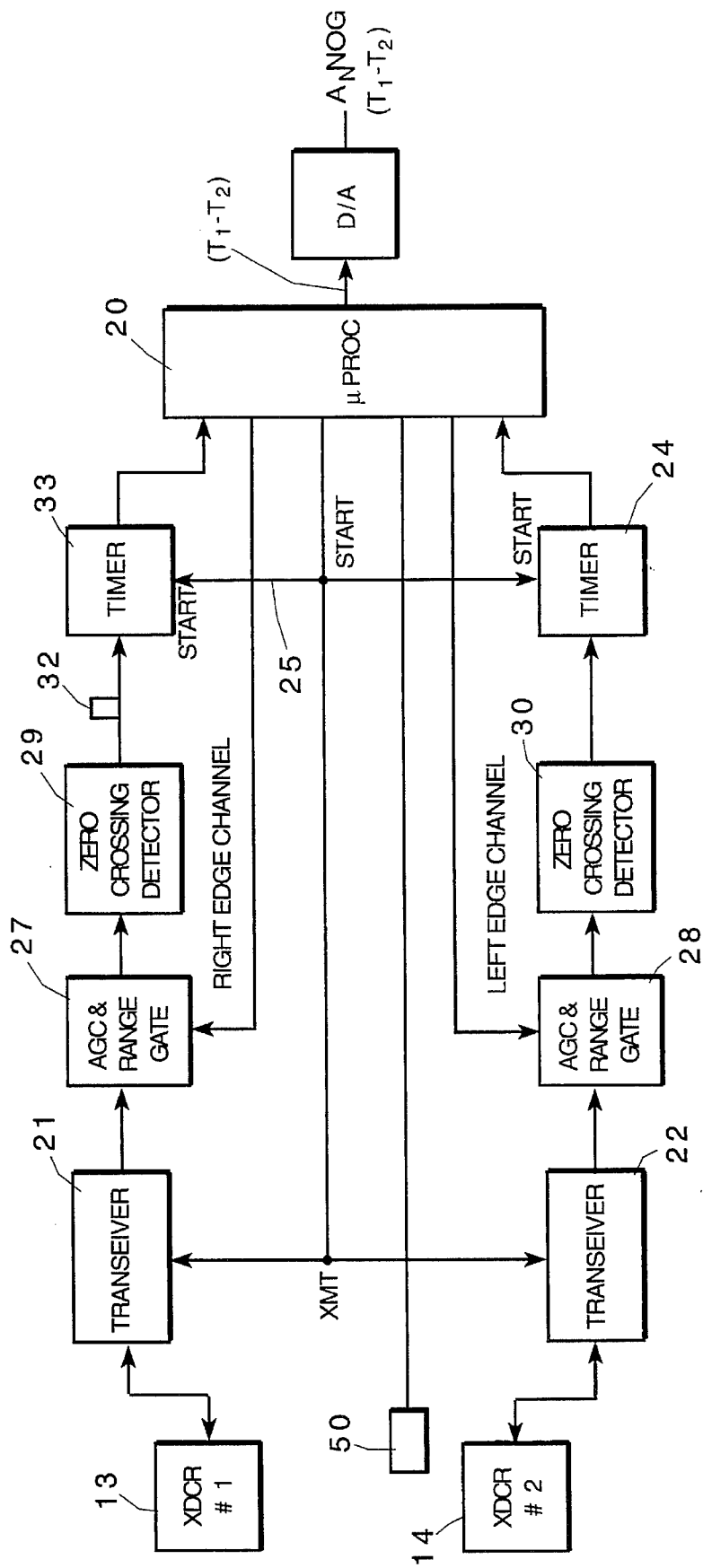
FIG. 3 is a block diagram of an electrical circuit incorporated in the invention, FIG. 4 lines A and B are electrical waveform and timing diagrams for the circuit shown in FIG. 3.

Referring now to the measuring circuit shown in FIG. 3, the right edge channel 16 and the left edge channel 17 are identical. Pulse power is delivered to the transducers 13 and 14 simultaneously, or in alternation. Preferably the transducers are operated at the same frequency, but this is not necessary. This is affected under control of microprocessor 20 sending start pulse to transceivers 21 and 22 and to initiate or start operation of timers 23 and 24, respectively. FIG. 4A and 4B waveform diagrams 40 show the start pulse 25 which is applied to start timer 23 and 24, and also constitutes the transmit start signal to transceivers 21 and 22 which, in turn, initiate the transmission of ultrasonic pulses 26 from each transducers 13 and 14, respectively. Reflections from the calibration targets CT are not shown for clarity of illustration.

Return ultrasonic signals are transduced by transducers 13 and 14, processed by transceivers 21 and 22. A range gate signal may be incorporated to cause the transceivers 21 and 22 to pass signals within a selected range or time interval (see FIGS. 7 and 8). The return ultrasonic signals are passed through conventional automatic gain control circuits 27 and 28 and conventional zero crossing detectors 29 and 30. As shown in the waveform diagrams of FIG. 4A, and FIG. 4B, ultrasonic signal 31 (one for the left edge LE channel and one for the right edge RE channel) applied to the zero crossing detectors 29 and 30 produce output pulses 32 (one for the left edge LE channel and one for the right edge RE channel) which are "stop" signals to timers 23 and 24, respectively. The time Ti is the time interval between transmission of the ultrasonic pulse signal 26 to return of signal due to diffraction at the left and right edges, respectively, of the strip 10.

These time intervals are received by microprocessor 20, which determines the time difference $T_1-T_2$ ($T_1$ being for one channel and $T_2$ being for the other channel) which is a measure of the change in the off-center portion of the strip 10 and becomes a control signal for repositioning mechanism 10. If strip positioning mechanism 11 requires an analog control signal, a digital-to-analog converter 35 is provided to provide an analog signal corresponding to the difference $T_1-T_2$. If $T_1-T_2$ is zero (0), and assuming symmetrical placement of the transducers, there has been no change in orientation of the edges LE and RE relative to centerline 11. If $T_1$ is the right edge channel time measurement, and is greater than $T_1$ ($T_1-T_2=T+$) then two things could have occurred: the strip 10 shifted to the right relative to centerline 11 ($T_2$ decreases as $T_1$ increases), or the strip 10 became wider on the right side, or both. If $T_2$ is the left edge channel time measurement, and $T_2$ is greater than $T_1$ ($T_1-T_2=T$) the strip either shifted to the left, or became wider on the left, or both. If the strip became wider on both sides simultaneously and remained centered, then $T_1-T_2$ would still be zero (0). Each of transducers 13 and 14 may be provided with a calibration target CT which is positioned at a predetermined distance from the transducer and used to convert time readings into distance.

The control signal is applied to positioning mechanism 12 to align the strip 10 with the centerline 12.

While the preferred embodiment uses time measurements, distance measurements can be done using the principles of the invention. In this case, the speed of sound in the medium is measured using techniques shown in my U.S. Pat. No. 4,938,066 or a separate temperature measurement and speed of sound computation as made by microprocessor 20.

If the height H of the transducers 13 and 14 above sheet 10 is known, microprocessor 20 can easily be programmed to calculate the width of the sheet. Accordingly, a further transducer 50 is mounted at the height of transducers 13 and 14 and makes a conventional ultrasonic measurement of the height H of the transducer above surface 15 of strip 10. A temperature measurement device 51 supplies a temperature reading to microprocessor 20 so that an accurate speed of sound factor is provided to make accurate distance measurements.

In some situations, there may not be enough space above the strip 10 to mount the transducer. In such case, they can be mounted below the strip in the same orientations shown in FIG. 2. However, in an alternative embodiment shown in FIG. 5, the transducers 13 and 14 (only one shown in FIG. 5 for simplicity of illustration) can be protected by a shield 60. In this case, an acoustic reflector 61 is positioned below the transducers to redirect the ultrasonic energy pulses toward the respective edges of sheet 10. Calibration targets 64 and 65 are positioned at a predetermined distance from each of the respective transducers 13' and 14'.

Figure 6:
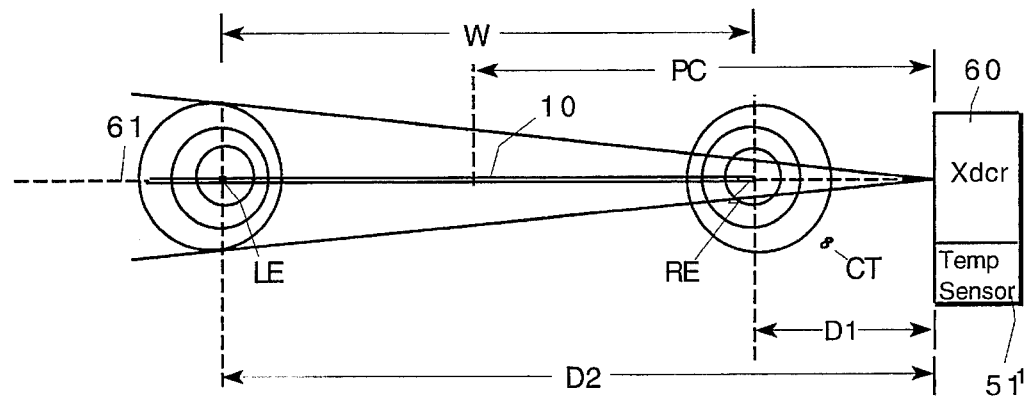
FIG. 6 illustrates a further alternative embodiment of the invention using a single ultrasonic transducer.
Figure 8:
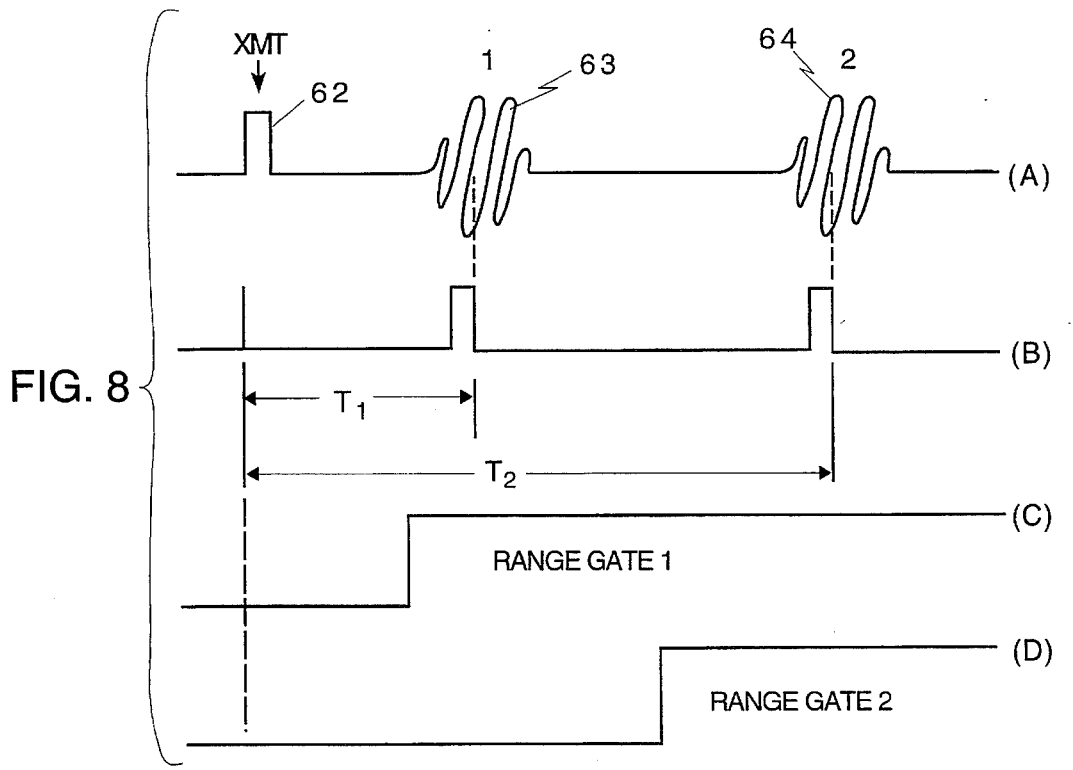

Referring now to the embodiment illustrated in FIG. 6, a single transducer 14' is mounted so that its acoustic axis 61 is collinear with the lateral axis of the thin strip 10. As shown in FIG. 6, the acoustic beam is wider than the thickness of the moving strip. In response to an acoustic pulse 62 (FIG. 8, line A) the near edge (right edge RE in FIG. 6) reflects a signal 63 back at transducer 14' at time $T_1$ and the far edge (left edge LE in FIG. 6) is insonified by the acositc pulse and diffracts a signal 64 back to transducer 14' arriving at time $T_2$ (FIG. 8, line B). A temperature measuring device 51' supplies an ambient temperature signal to microprocessor 20' via signal conditioning circuit 51TC. Microprocessor 20 uses the temperature measurement in conjunction with the signal from calibration target CT to compute the speed of sound (C) and subsequently to compute the distances $D_1$ and $D_2$ using known formulas and output the following quantities:

| | |
|---|---|
| Center distance | $D_c = \frac{1}{2}(D_1 + D_2)$ |
| Strip width (W) | $W = D_2 - D_1$ |

Figure 7:
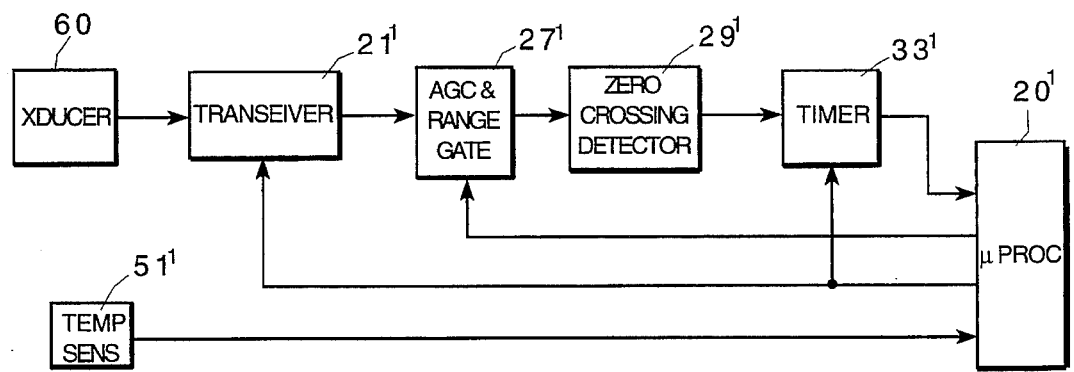
FIG. 7 is a block diagram of a further electrical circuit incorporated in the invention, and FIG. 8 lines A, B, C and D are electrical waveform and timing diagrams for the embodiment shown in FIG. 6.

In the embodiment illustrated in FIGS. 6 and 7, one timer 23' is used with different range gates (FIG. 8, line C and FIG. 8, line D) on alternate pulse measurements. The time measurements can also be made using two timers on every cycle with a different range gate (FIGS. 8, line C and 8, line D) for each timer.

While preferred embodiments of the invention have been shown and described, it will be appreciated that other embodiments and adaptations of the invention will be readily apparent to those skilled in the art and still be within the spirit and scope of the invention.

What is claimed is:

1. A system for locating the positions of the edges of a moving strip of material having two edges, comprising:
   a pair of ultrasonic transducers positioned adjacent the path of said moving strip,
   one of said ultrasonic transducers being oriented in a direction at an acute angle toward one of said two edges and the other of said ultrasonic transducers being oriented in a direction at said acute angle toward the other edge of said two edges,
   first circuit means for causing each of said transducers to emit a beam of ultrasonic pulses in air in the directions of said two edges, respectively, to insonify said two edges, second circuit means connected to said ultrasonic transducers for detecting acoustic diffractions and determining the times of detection caused by said two edges, respectively, and means for comparing the times of detection of said acoustic diffractions to locate the positions of said edges relative to said pair of transducers.

2. A system for measuring the width of a moving strip of material comprising the system for locating the positions of the edges of a moving strip of material as defined in claim 1 and ultrasonic ranging means for measuring the height of said transducers above said moving strip of material and means for computing the width of said moving strip of material from the height measurement from said ultrasonic ranging means and the positions of said edges relative to said pair of ultrasonic transducers.

3. A system for maintaining a moving steel strip centered at a given point comprising the system for locating the positions of the edges defined in claim 1 and motive means connected to said second circuit means for shifting said strip relative to said pair of ultrasonic transducers to eliminate any difference in the positions of said edges relative to said pair of ultrasonic transducer.

4. A system for locating at least one edge of a moving strip of material having a reflective surface, comprising:

an ultrasonic transducer positioned adjacent the path of said moving strip, and oriented at an acute angle toward said at least one edge so that an acoustic pressure wave is transmitted on top of the surface of said strip through air, circuit means for causing said transducer to emit ultrasonic pulse in air at a time T on top of said surface of said strip and in the direction of said at least one edge, and detector means connected to said ultrasonic transducer for detecting acoustic diffractions caused by said at least one edge, and means for determining the location of said at least one edge from the time T of emission of said ultrasonic pulse and time of detection of said acoustic diffractions.

5. A system for locating edges of a moving linear strip of material having a thickness and pair of edges, comprising:

an ultrasonic transducer having anultrasonic beam with a width wider than the thickness of said strip and positioned and oriented at an angle of 0 or at an acute angle toward at least one edge of said strip so that at a time T an acoustic pressure wave is transmitted on top of at least one surface of said strip through the air, circuit means for causing said transducer to emit an ultrasonic pressure wave through the air and on top of said at least one surface of said strip and in the direction of said at least one edge, and detector means connected to said ultrasonic transducer for detecting acoustic diffractions caused by said pressure wave passing said at least one edge, and means for determining the location of said at least one edge from the time T of emission of said ultrasonic pulse and time of detection of said diffractions.

6. The system defined in claim 5 wherein said strip has near and far edges and a lateral axis and said ultrasonic transducer is oriented substantially collinear with said lateral axis and opposite the near one of said two edges.

7. The system defined in claim 6, said detector means including microprocessor means for controlling operation of said transducer and receiving signals therefrom and computing at least one of the following quantities:

1) the distance from said transducer to said near one of said two edges, 2) the distance from said transducer to the far one of said two edges, 3) the distance to the center of said strip from said transducer, and 4) the width of said strip.

* * * * *